DEFENSIVE PUBLICATION

UNITED STATES PATENT AND TRADEMARK OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent and Trademark Office makes no assertion as to the novelty of the disclosed subject matter.

PUBLISHED FEBRUARY 3, 1976

943 O.G. 76

T943,010

FOAMABLE CHLORHEXIDINE-CONTAINING SYSTEM

Nicholas Rocko Pettoruto, Wilmington, Del., assignor to ICC United States Inc., Wilmington, Del.

Filed Sept. 18, 1974, Ser. No. 507,196

Int. Cl. A61k *31/205*

U.S. Cl. 424—316

No Drawing. 9 Pages Specification

An aqueous, foamable chlorhexidine-nonionic/cationic surfactant system is presented which can be used to form germicidal foams over long periods of time. Aqueous systems containing chlorhexidine [1,6-di-(4-chlorophenylidiguanido)hexane] salts are combined with nonionic or cationic surfactants having an HLB of at least 10 and preferably in the range of 12–18. Preferred surfactants are selected from combinations of polyoxyethylene ethers or partial hexitan esters of fatty acids having 12–24 carbon atoms, fatty alcohols, and polyoxyethylene derivatives of fatty alcohols having 10–18 carbon atoms, polyhydric materials such as sorbitol and carboxyl-vinyl polymers are included.